United States Patent [19]
Latimer et al.

[11] Patent Number: 6,079,273
[45] Date of Patent: Jun. 27, 2000

[54] EMAT INSPECTION OF HEADER TUBE STUBS

[75] Inventors: Paul J. Latimer; Charles B. Overby, both of Campbell County, Va.; Ralph D. Murphy, Akron, Ohio

[73] Assignees: McDermott Technology, Inc.; The Babcock & Wilcox Company, both of New Orleans, La.

[21] Appl. No.: 09/069,445

[22] Filed: Apr. 29, 1998

[51] Int. Cl.[7] .................................................. G01N 29/04
[52] U.S. Cl. .............................................. 73/622; 73/643
[58] Field of Search ............................ 73/599, 600, 620, 73/622, 627, 629, 637, 638, 643

[56] References Cited

U.S. PATENT DOCUMENTS

| | | | |
|---|---|---|---|
| 4,312,231 | 1/1982 | Kawashiima et al. | 73/643 |
| 4,685,334 | 8/1987 | Latimer | 73/622 |
| 5,035,143 | 7/1991 | Latimer | 73/598 |
| 5,526,691 | 6/1996 | Latimer et al. | 73/598 |
| 5,619,423 | 4/1997 | Scrantz | 73/622 |

*Primary Examiner*—Hezron Williams
*Assistant Examiner*—Rose M. Miller
*Attorney, Agent, or Firm*—Robert J. Edwards; Eric Marich; Robert C. Baraona

[57] ABSTRACT

A method for non-destructively testing closely-spaced objects, such as header tube stubs for a furnace or boiler using electromagnetic acoustic transducers (EMATs) having meander coil sensors. The small size of the sensor combined with the need to move the sensor only a small fraction of the circumference of a tube to scan the entire circumference of the tube under test permits easy and accurate testing of an entire tube, even when the tube is one of a closely-spaced bundle.

10 Claims, 3 Drawing Sheets

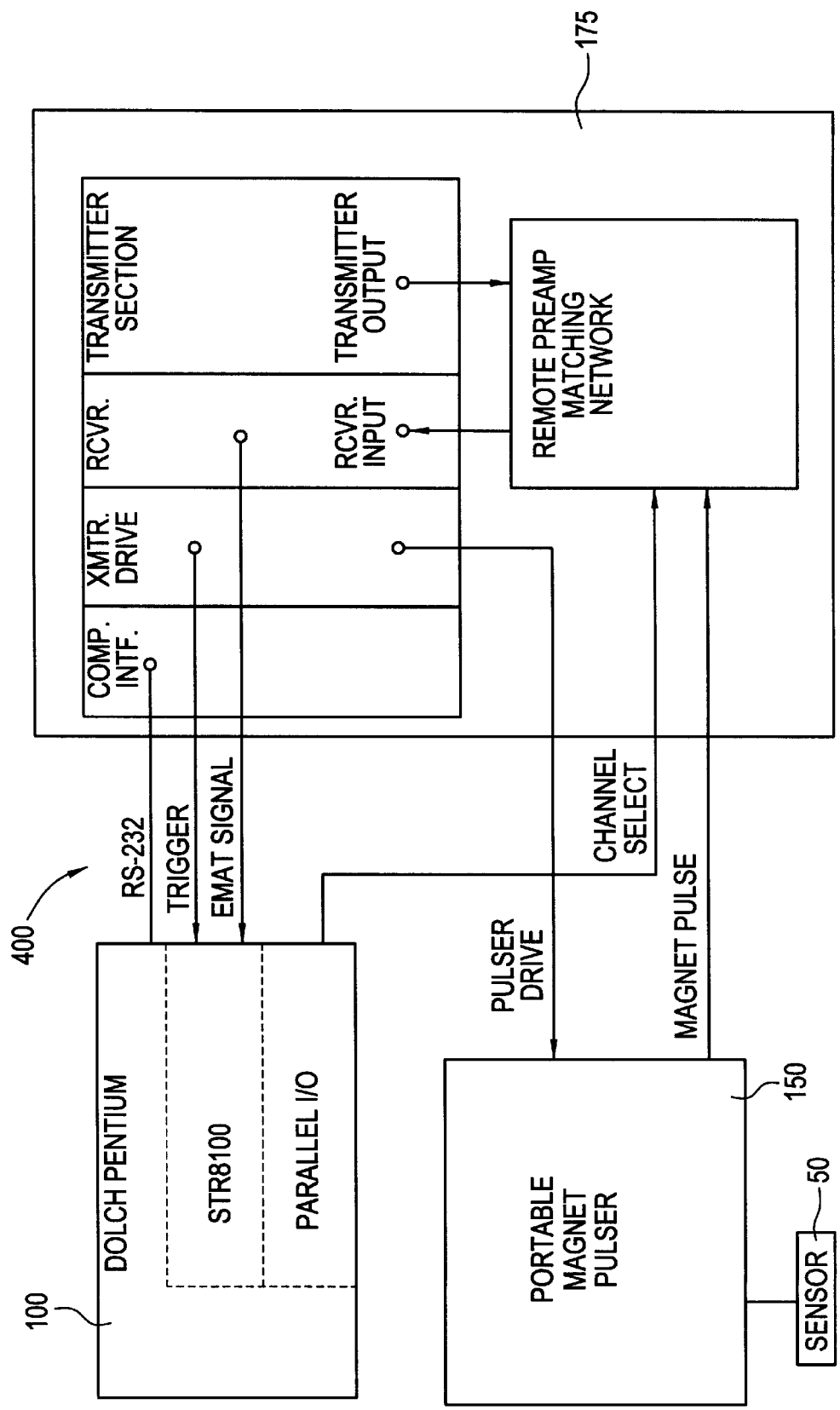

EMAT INSPECTION OF HEADER TUBE STUBS

FIELD AND BACKGROUND OF THE INVENTION

The present invention relates generally to the field of non-destructive testing and, in particular, to a new and useful method for testing boiler and furnace header tube stubs using electromagnetic acoustic transducer (EMAT) technology.

Latimer et al. (U.S. Pat. No. 5,035,143) discloses a method for ultrasonically detecting creep swelling in tubular members such as fossil utility steam lines and headers. Either standard piezoelectric transducers or EMATs can be used to generate the ultrasonic waves.

Ultrasonic inspection of header tube stubs, among other locations in an industrial furnace or boiler, is difficult using conventional ultrasound techniques. Conventional ultrasound techniques using piezoelectric transducers require a critical alignment of the transducer with the object under test. Adequate couplant must be maintained between the ultrasonic transducer and the object, and access is limited in many areas where the operator may be reaching through several tube banks. In addition, a conventional ultrasonic inspection using a piezoelectric transducer must scan completely around the tube stub, a task which is sometimes virtally impossible considering the problems of access, alignment, and maintaining adequate couplant. For these reasons, there is presently no known method for conducting a complete ultrasound technology assessment of boiler and furnace tube stubs and headers.

SUMMARY OF THE INVENTION

It is an object of the present invention to provide a method for non-destructively testing closely arranged objects in a boiler or furnace.

It is a further object of the invention to provide a testing method for non-destructively assessing the tube stubs along an entire length of a header and tube stub arrangement in a boiler or furnace.

Accordingly, one aspect of the present invention is drawn to a method for non-destructively inspecting an arrangement of closely spaced objects using an electromagnetic acoustic transducer (EMAT). The method comprises the steps of: providing an arrangement of closely-spaced objects for inspection; providing an electromagnetic acoustic transducer (EMAT) having a meander coil sensor; locating the meander coil sensor of the EMAT at a first location in close proximity to one of the closely-spaced objects; activating the EMAT to produce a transit signal in the one of the closely-spaced objects; and sensing the presence of a flaw signal generated by the reflection of the transit signal from a flaw in the one of the closely-spaced objects with the EMAT meander coil sensor and producing a signal indicative thereof.

A condition assessment of a boiler or furnace header can thus be performed using an electromagnetic acoustic transducer (EMAT). Tube stubs connected to the header are inspected, starting from outer ends of the header and moving inwardly toward the center, until there is no longer detectable damage. This method allows an assessment of the total damage, if any, to the header.

The inspection steps of the method include placing an appropriately sized EMAT sensor on each of the tube stubs and moving it circumferentially a small distance or fraction of the total circumference (about 1") while observing a display screen output for an indication of the presence of cracks. By using EMATs, according to the present invention, the operator only has to place the sensor at one position on the tube and move the EMAT slightly away therefrom (preferably, circumferentially) to inspect the dead zone under the EMAT sensor coil and 180° away.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 4 is an electromechanical schematic diagram of an EMAT system configuration used with the method of the invention.

DESCRIPTION OF THE PREFERRED EMBODIMENTS

Figure 1:
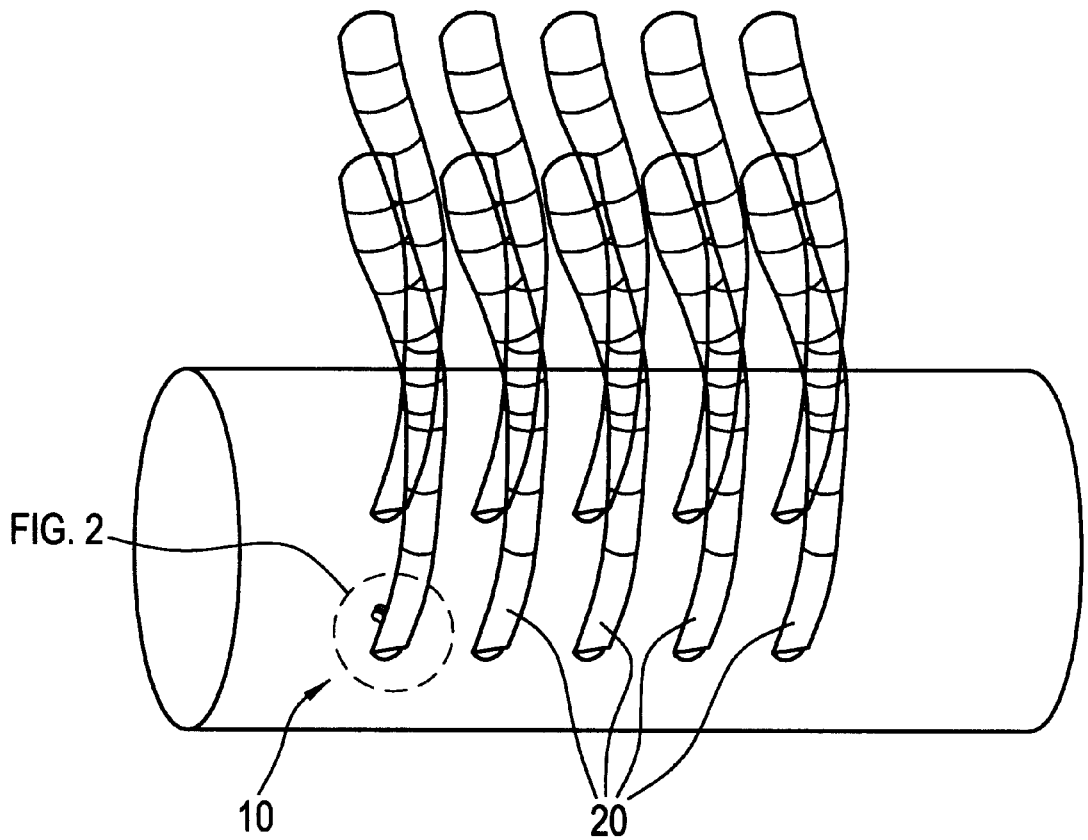
FIG. 1 is a perspective drawing of a header and attached tube stubs of the type used in boilers and furnaces.

Referring now to the drawings, in which like reference numerals designate the same or functionally similar elements, FIG. 1 shows a header 10, such as that found in a furnace or boiler (not shown) to which is connected a plurality of closely spaced tube stubs 20 extending outwardly from the header 10.

Figure 2:
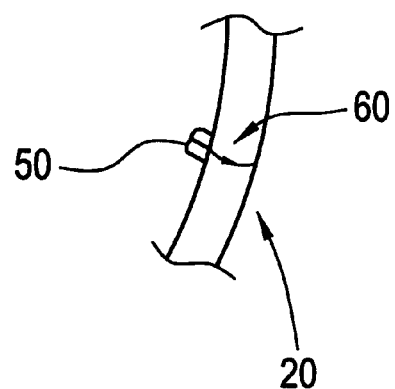
FIG. 2 is an enlargement of the section of FIG. 1 identified as "2", illustrating the placement of an electromagnetic acoustic transducer (EMAT) positioned adjacent to a tube stub.

An enlargement of section 2 of FIG. 1 is illustrated in FIG. 2. As illustrated, tube stub 20 has a meander coil EMAT sensor 50 positioned in close proximity. In order for a human operator to use EMAT sensor 50 in the small spaces between the tube stubs 20 on header 10, the EMAT sensor 50 is preferably sized to be about 1"–2" high, although other sizes may be used if the spacing between the tube stub 20 elements is adequate.

The EMAT sensor 50 is used to both send and receive ultrasonic pulses to and from the tube stub 20. It incorporates a transmitter/receiver coil for generating eddy currents in the tube stub 20. Lorentz forces resulting from the interaction of the eddy currents with a magnetic field generated by the EMAT sensor 50 cause an ultrasonic wave to be generated. The ultrasonic wave propagates circumferentially around the tube stub 20 in the direction 60. EMAT sensor 50 then detects/receives the ultrasonic wave and produces a signal indicative thereof which is transmitted back to EMAT circuitry 400 (shown in FIG. 4) for analysis and display. The header 10 may be tested in a similar manner.

Figure 3:
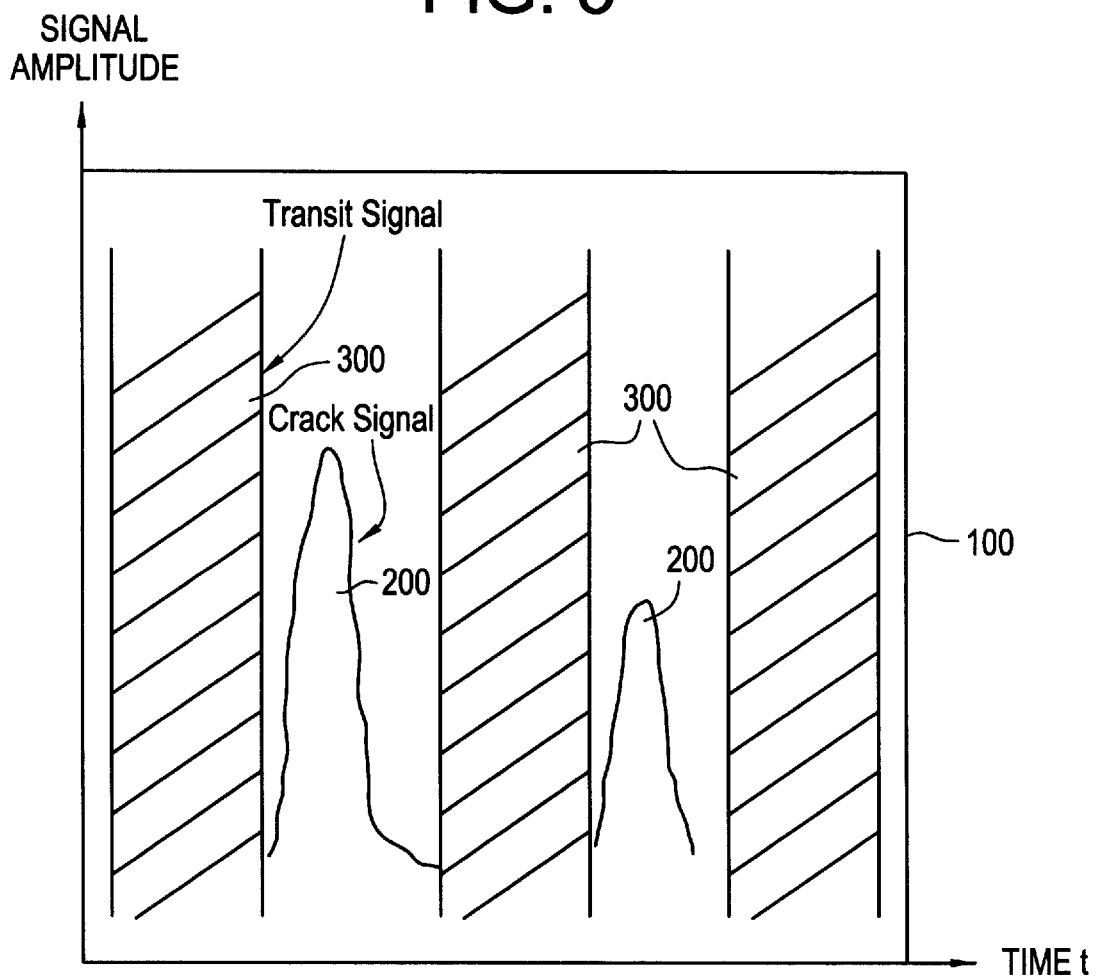
FIG. 3 is a representation of signals received by the EMAT sensor used to detect a flaw.

FIG. 3 is a representation of an output observed on a computer or oscilloscope screen 100. Transit signals 300 result when the ultrasonic shear wave produced by the EMAT sensor 50 travels completely around the circumference of the tube stub 20. This is possible with EMATs because they are bidirectional and thus can either transmit or receive from either end of the sensor. This is not possible with conventional piezoelectric sensors.

When the ultrasound from the EMAT sensor 50 encounters a crack, part of the sound is reflected back to the EMAT sensor 50 and the other part of the sound continues to complete the transit around the tube stub 20. The reflected component is received as a flaw signal 200 and will thus appear inbetween the transit signals 300 because the total time of flight from the EMAT sensor 50 to the flaw and back is less than the time to go completely around the tube stub 20. Therefore, the signals appearing between the transit signals 300 are the flaw signals 200.

An EMAT inspection system configuration 400 used with the method is schematically illustrated in FIG. 4. A small pulsed magnet 150 is connected to a multistrand meander coil EMAT sensor 50 to produce vertically polarized (SV) shear waves around the circumference of the tube stub 20. Since EMATs are bidirectional, a complete trip or transit around the tube stub 20 can be detected by the meander coil EMAT sensor 50. The pulser-receiver 175 is operated in a pulse-echo mode, the selection and operation of which is well-known to those skilled in the art of EMAT testing. In this mode, there is always a dead zone directly under the EMAT sensor 50 transmitter due to the initial pulse excitation. Therefore it is necessary to move the EMAT sensor 50 a small amount to ensure a complete inspection of the test object. However, the small size of this EMAT sensor 50, as described above, allows the EMAT sensor 50 to be located as necessary about the header tube stub 20, thus ensuring a highly reliable inspection.

The close proximity of the tube stubs 20 to the header 10 is the major difficulty encountered in performing any inspection of this type. In one test, the inspection system 400 and EMAT sensor 50 were initially calibrated on a 0.050" notch in a tube 20 of similar diameter and wall thickness. In these trials, a frequency of 2 MHz was used; other frequencies could be used for higher resolution, if desired. The flaw signal 200 from a crack in a header tube stub 20 was then easily found as an increase in amplitude between the complete transit signals 300. In practice, the signal was located between the first and second transit signals 300. The extent of the initial pulse excitation prevented the detection of the crack before the first transit signal 300 in time. The orientation is favorable for detection of longitudinal cracks which is the expected orientation of such cracks in header tube stubs.

Experimentation with the technique has demonstrated that it can detect cracks in header tube stubs in both the laboratory and in actual fossil utility environments in the field. It should be observed that while the method has been described for use with furnace or boiler components, the inspection method is also applicable to inspection of other closely-arranged objects or curved objects which are not conducive to maintaining constant contact required by other ultrasound technology inspection devices. Further, different sensor constructions or arrangements enable different inspection techniques to be employed with the method of the present invention. For example, a permanent magnet could be used instead of a pulsed magnet. Also, a pitch-catch EMAT arrangement could be used; in this case, the EMAT would be provided with separate transmitter and receiver coils, located either one on top of the other or side-by-side one another. A pitch-catch approach could be quite useful in the present method because the initial pulse excitation would be somewhat reduced. Thus, while a specific embodiment of the invention has been shown and described in detail to illustrate the application of the principles of the invention, it will be understood that the invention may be embodied otherwise without departing from such principles.

We claim:

1. A method for non-destructively inspecting an arrangement of closely spaced cylindrical objects using an electromagnetic acoustic transducer (EMAT), comprising the steps of:

providing for inspection an arrangement of closely-spaced cylindrical objects, each object having a circumference;

providing an electromagnetic acoustic transducer (EMAT) having a meander coil sensor;

locating the meander coil sensor of the EMAT at a first location in close proximity to one of the closely-spaced cylindrical objects;

activating the EMAT to produce a transit signal in the one of the closely-spaced cylindrical objects;

sensing the presence of a flaw signal generated by the reflection of the transit signal from a flaw in the one of the closely-spaced objects with the EMAT meander coil sensor and producing a signal indicative thereof; and circumferentially moving the EMAT meander coil sensor a distance from the first location to a second location along the circumference of one of the closely-spaced cylindrical objects in order to obtain a complete scan of the cross-section directly beneath the EMAT meander coil sensor on the one of the closely-spaced cylindrical objects under inspection.

2. The method according to claim 1, comprising the step of displaying the signal indicative of the flaw on display means.

3. The method according to claim 1, comprising the step of providing an arrangement of closely-spaced header tube stubs for inspection.

4. The method according to claim 1, comprising the step of operating the EMAT in a pulse-echo mode.

5. The method according to claim 1, comprising the steps of providing two meander coils in the EMAT, one a transmitter coil and the other a receiver coil, and operating the EMAT in a pitch-catch mode.

6. The method according to claim 5, comprising the step of providing the two meander coils one on top of the other in the EMAT.

7. The method according to claim 5, comprising the step of providing the two meander coils side-by-side one another in the EMAT.

8. The method according to claim 1, further comprising the step of, subsequent to the circumferentially moving step, longitudinally moving the EMAT meander coil sensor a distance from the second location along the length of the one of the closely-spaced cylindrical objects in order to obtain a complete scan of the entire length and cross-section of the one of the closely-spaced cylindrical objects under inspection.

9. A method for nondestructively inspecting an arrangement of closely-spaced header tube stubs using an electromagnetic acoustic transducer (EMAT), comprising the steps of:

providing a header having an arrangement of closely-spaced header tube stubs for inspection;

providing an electromagnetic acoustic transducer (EMAT) having a meander coil sensor;

locating the meander coil sensor of the EMAT at a first location in close proximity to one of the closely-spaced header tube stubs;

activating the EMAT to produce a transit signal in one of the closely-spaced header tube stubs;

sensing the presence of a flaw signal generated by the reflection of the transit signal from a flaw in the one of the header tube stubs with the EMAT meander coil sensor and producing a signal indicative thereof; and moving the EMAT meander coil sensor a distance from the first location equal to a fraction of a circumference of one of the closely-spaced header tube stubs to obtain a complete scan of the one of the closely-spaced header tube stubs under inspection.

10. A method according to claim 1 comprising the steps of providing an EMAT which is less than 2 inches high.

* * * * *